United States Patent
Schnabel et al.

Patent Number: 5,747,421
Date of Patent: May 5, 1998

[54] FORMYLAMINOPHENYLSULFONYLUREAS, PREPARATION PROCESSES AND USE AS HERBICIDES AND PLANT GROWTH REGULATORS

[75] Inventors: Gerhard Schnabel, Großwallstadt; Lothar Willms, Hofheim; Klaus Bauer, Hanau; Hermann Bieringer, Eppstein; Christopher Rosinger, Hofheim, all of Germany

[73] Assignee: Hoechst Schering Agrevo GmbH, Berlin, Germany

[21] Appl. No.: 453,978

[22] Filed: May 30, 1995

[30] Foreign Application Priority Data

Jun. 1, 1994 [DE] Germany .............. 44 19 259.2
Mar. 20, 1995 [DE] Germany .............. 195 10 078.6

[51] Int. Cl.$^6$ .................. C07D 239/69; A01N 43/54
[52] U.S. Cl. .................. 504/214; 504/215; 544/321; 544/323; 544/324; 544/331; 544/332; 544/122; 544/123
[58] Field of Search ............. 504/214, 215; 544/321, 323, 324, 331, 332, 122, 123

[56] References Cited

U.S. PATENT DOCUMENTS

| | | | |
|---|---|---|---|
| 4,632,695 | 12/1986 | Schurter et al. | 544/211 |
| 4,664,695 | 5/1987 | Schurter et al. | 544/321 |
| 4,892,946 | 1/1990 | Levitt | 544/321 |
| 4,981,509 | 1/1991 | Hillemann | 544/208 |
| 5,157,119 | 10/1992 | Campopiano et al. | 544/211 |

FOREIGN PATENT DOCUMENTS

| | | |
|---|---|---|
| 0001515 | 4/1979 | European Pat. Off. |
| 0044807 | 1/1982 | European Pat. Off. |
| 0116518 | 8/1984 | European Pat. Off. |
| 0166516 | 1/1986 | European Pat. Off. |
| 0232067 | 8/1987 | European Pat. Off. |
| 42 36 902 | 5/1994 | Germany |
| 43 22 067 | 1/1995 | Germany |
| WO 94/10154 | 5/1994 | WIPO |

*Primary Examiner*—John M. Ford
*Attorney, Agent, or Firm*—Frommer Lawrence & Haug LLP

[57] ABSTRACT

Formylaminophenylsulfonylureas; processes for their preparation, and their use as herbicides and plant growth regulators Compounds of the formula (I)

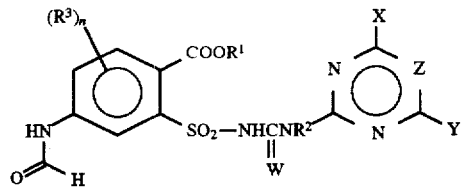

in which

R$^1$ is H, a substituted or unsubstituted hydrocarbon radical or an unsubstituted or substituted heterocyclic radical, R$^2$ is H, (C$_1$–C$_6$)-alkyl or (C$_1$–C$_6$)-alkoxy, R$^3$ is halogen, (C$_1$–C$_6$)-alkyl, (C$_1$–C$_6$)-alkoxy, (C$_1$–C$_6$)-haloalkyl, (C$_1$–C$_6$)-haloalkoxy, NO$_2$, CN, NH$_2$, (C$_1$–C$_4$) -mono- or dialkylamino, each independently of other radicals R$^3$ if n is 2 or 3, n is 0, 1, 2 or 3, W is an oxygen atom or a sulfur atom, X and Y independently of one another are halogen, (C$_1$–C$_6$)-alkyl, (C$_1$–C$_6$)-alkoxy or (C$_1$–C$_6$)-alkylthio, each of the three last-mentioned radicals being unsubstituted or substituted by one or more radicals selected from the group consisting of halogen, (C$_1$–C$_4$)-alkoxy and (C$_1$–C$_4$)-alkylthio, or are (C$_3$–C$_6$)-cycloalkyl, (C$_2$–C$_6$)-alkenyl, (C$_2$–C$_6$)-alkynyl, (C$_2$–C$_6$)-alkenyloxy, (C$_2$–C$_6$)-alkynyloxy, mono- or di[(C$_1$–C$_4$-alkyl)]amino, and Z is CH or N, are suitable as herbicides and plant growth regulators. The compounds (I) can be prepared by processes analogous to known processes whereby some novel intermediates of formula (II) are used.

17 Claims, No Drawings

FORMYLAMINOPHENYLSULFONYLUREAS, PREPARATION PROCESSES AND USE AS HERBICIDES AND PLANT GROWTH REGULATORS

The invention is in the technical field of herbicides and plant growth regulators, in particular of herbicides for the selective control of broad-leaved weeds and grass weeds in crops of useful plants.

It has been disclosed that heterocyclically substituted phenylsulfonylureas which have an amino group or functionalized amino group attached to the phenyl ring have herbicidal and plant growth-regulating properties; see EP-A-1515, U.S. Pat. No. 4,892,946, U.S. Pat. No. 4,981,509, DE-A-4322067, EP-A-116 518 (=U.S. Pat. No. 4,664,695, U.S. Pat. No. 4,632,695), DE-A-4236902 (WO 94/10154).

Surprisingly, it has now been found that certain substituted N-(aminophenylsulfonyl)-N'-(pyrimidinyl- or -triazinyl)ureas are particularly suitable for use as herbicides or plant growth regulators.

The present invention relates to compounds of the formula (I),

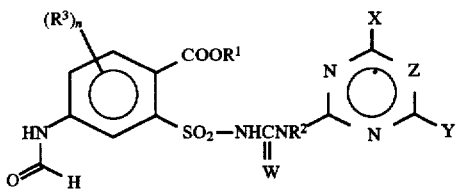

in which

R$^1$ is H, a substituted or unsubstituted hydrocarbon radical or an unsubstituted or substituted heterocyclic radical, R$^2$ is H, (C$_1$–C$_6$)-alkyl or (C$_1$–C$_6$)-alkoxy, R$^3$ is halogen, (C$_1$–C$_6$)-alkyl, (C$_1$–C$_6$)-alkoxy, (C$_1$–C$_6$)-haloalkyl, (C$_1$–C$_6$)-haloalkoxy, NO$_2$, CN, NH$_2$ or (C$_1$–C$_4$)-mono- or dialkylamino, each independently of other radicals R$^3$ if n is 2 or 3, n is 0, 1, 2 or 3, W is an oxygen atom or a sulfur atom, X and Y independently of one another are halogen, (C$_1$–C$_6$)-alkyl, (C$_1$–C$_6$)-alkoxy or (C$_1$–C$_6$)-alkylthio, each of the three last-mentioned radicals being unsubstituted or substituted by one or more radicals selected from the group consisting of halogen, (C$_1$–C$_4$)-alkoxy and (C$_1$–C$_4$)-alkylthio, or are (C$_3$–C$_6$)-cycloalkyl, (C$_2$–C$_6$)-alkenyl, (C$_2$–C$_6$)-alkynyl, (C$_2$–C$_6$)-alkenyloxy, (C$_2$–C$_6$)-alkynyloxy, mono- or di[(C$_1$–C$_4$)-alkyl]amino, and Z is CH or N.

In formula (I) and in all subsequent formulae, the radicals alkyl, alkoxy, haloalkyl, haloalkoxy, alkylamino and alkylthio and the corresponding unsaturated and/or substituted radicals in the hydrocarbon skeleton can in each case be straight-chain or branched. Unless specifically indicated, preferred radicals amongst these are the lower carbon skeletons, for example having 1 to 4 carbon atoms or, in the case of unsaturated groups, 2 to 4 carbon atoms. Alkyl radicals, also in the composite meanings such as alkoxy, haloalkyl and the like, are, for example, methyl, ethyl, n- or i-propyl, n-, i-, t- or 2-butyl, pentyl radicals, hexyl radicals such as n-hexyl, i-hexyl and 1,3-dimethylbutyl, heptyl radicals such as n-heptyl, 1-methylhexyl and 1,4-dimethylpentyl; alkenyl and alkynyl radicals have the meaning of the possible unsaturated radicals which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl and 1-methylbut-3-yn-1-yl.

Halogen is, for example, fluorine, chlorine, bromine or iodine. Haloalkyl, haloalkenyl and haloalkynyl are alkyl, alkenyl and alkynyl, each of which is partially or fully substituted by halogen, preferably by fluorine, chlorine and/or bromine, in particular by fluorine or chlorine, and is, for example, CF$_3$, CHF$_2$, CH$_2$F, CF$_3$CF$_2$, CH$_2$FCHCl, CCl$_3$, CHCl$_2$ or CH$_2$CH$_2$Cl; haloalkoxy is, for example, OCF$_3$, OCHF$_2$, OCH$_2$F, CF$_3$CF$_2$O, OCH$_2$CF$_3$ and OCH$_2$CH$_2$Cl; the same applies analogously to haloalkenyl and other halogen-substituted radicals.

A hydrocarbon radical is a straight-chain, branched or cyclic and saturated or unsaturated aliphatic or aromatic hydrocarbon radical, for example alkyl, alkenyl, alkynyl, cycloalkyl, cycloalkenyl or aryl; aryl is a mono-, di- or polycyclic aromatic system, for example phenyl, naphthyl, tetrahydronaphthyl, indenyl, indanyl, pentalenyl, fluorenyl and the like, preferably phenyl; a hydrocarbon radical is preferably alkyl, alkenyl or alkynyl having up to 12 carbon atoms or cycloalkyl having 5 or 6 ring atoms, or phenyl;

A heterocyclic radical or ring can be saturated, unsaturated or heteroaromatic; it has one or more hetero ring atoms, preferably selected from the group consisting of N, O and S; it is preferably 5- or 6-membered and has 1, 2 or 3 hetero ring atoms. For example, the heterocyclic radical can be a heteroaromatic radical or ring (heteroaryl), such as, for example, a mono-, di- or polycyclic aromatic system in which at least 1 ring has one or more hetero atoms, for example pyridyl, pyrimidinyl, pyridazinyl, pyrazinyl, thienyl, thiazolyl, oxazolyl, furyl, pyrrolyl, pyrazolyl and imidazolyl, or it is a partially hydrogenated radical such as oxiranyl, pyrrolidyl, piperidyl, piperazinyl, dioxolanyl, morpholinyl or tetrahydrofuryl. Suitable substituents for a substituted heterocyclic radical are the substituents mentioned further below, and additionally also oxo. The oxo group can also occur on those hetero ring atoms of which various degrees of oxidation are possible, for example in the case of N and S.

Substituted radicals, such as substituted hydrocarbon radicals, for example substituted alkyl, alkenyl, alkynyl, aryl, phenyl and benzyl, or substituted heteroaryl, are, for example, a substituted radical which is derived from the unsubstituted parent structure, the substituents being, for example, one or more, preferably 1, 2 or 3, radicals selected from the group consisting of halogen, alkoxy, haloalkoxy, alkylthio, hydroxy, amino, nitro, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl, and, in the case of cyclic radicals, also alkyl and haloalkyl, as well as unsaturated aliphatic radicals, such as alkenyl, alkynyl, alkenyloxy, alkynyloxy and the like, which correspond to the above-mentioned saturated hydrocarbon-containing radicals. Preferred amongst the radicals which have carbon atoms are those having 1 to 4 carbon atoms, in particular 1 or 2 carbon atoms. As a rule, preferred substituents are those selected from the group consisting of halogen, for example fluorine and chlorine, (C$_1$–C$_4$)-alkyl, preferably methyl or ethyl, (C$_1$–C$_4$)-haloalkyl, preferably trifluoromethyl, (C$_1$–C$_4$)-alkoxy, preferably methoxy or ethoxy, (C$_1$–C$_4$)-haloalkoxy, nitro and cyano. Particularly preferred are the substituents methyl, methoxy and chlorine.

Optionally substituted phenyl is preferably phenyl which is unsubstituted or mono- or polysubstituted, preferably up to trisubstituted, by identical or different radicals selected from the group consisting of halogen, $(C_1-C_4)$-alkyl, $(C_1-C_4)$-alkoxy, $(C_1-C_4)$-haloalkyl, $(C_1-C_4)$-haloalkoxy and nitro, for example o-, m- and p-tolyl, dimethylphenyl radicals, 2-, 3- and 4-chlorophenyl, 2-, 3- and 4-trifluoro- and -trichlorophenyl, 2,4-, 3,5-, 2,5- and 2,3-dichlorophenyl, and o-, m- and p-methoxyphenyl.

An acyl radical is the radical of an organic acid, for example the radical of a carboxylic acid and radicals of acids derived therefrom, such as thiocarboxylic acid, optionally nitrogen-substituted iminocarboxylic acids, or the radical of carbonic monoesters, optionally nitrogen-substituted carbamic acid, sulfonic acids, sulfinic acids, phosphonic acids, phosphinic acids. Acyl is, for example, formyl, alkylcarbonyl such as [$(C_1-C_4$-alkyl)]-carbonyl, phenylcarbonyl, it being possible for the phenyl ring to be substituted, for example as shown above for phenyl, or alkoxycarbonyl, phenoxycarbonyl, benzoxycarbonyl, alkylsulfonyl, alkylsulfinyl, N-alkyl-1-iminoalkyl and other radicals of organic acids.

The invention also relates to all stereoisomers which are embraced by formula (I), and to mixtures of these. Such compounds of the formula (I) have one or more asymmetric carbon atoms or else double bonds, which are not mentioned specifically in the formulae (I). The stereoisomers which are possible, defined by their specific spatial form, such as enantiomers, diastereomers and Z and E isomers, are all embraced by the formula (I) and can be obtained by customary methods from mixtures of the stereoisomers, or else prepared by stereoselective reactions in combination with the use of stereochemically pure starting materials.

Compounds of the formula (I) according to the invention which are of particular interest are those in which $R^1$ is hydrogen, an aliphatic or cycloaliphatic hydrocarbon radical having up to 24 carbon atoms which is unsubstituted or substituted, or an unsubstituted or substituted saturated heterocyclic radical having 3 to 7 ring atoms, preferably H, $(C_1-C_6)$-alkyl, $(C_2-C_6)$-alkenyl, $(C_2-C_6)$-alkynyl or $(C_3-C_6)$-cycloalkyl, each of the four last-mentioned radicals being unsubstituted or substituted by one or more radicals selected from the group consisting of halogen, CN, $C_1-C_3$-alkoxy, $C_1-C_3$-haloalkoxy, $(C_3-C_6)$-cycloalkyl, $(C_1-C_3)$-alkylthio, $(C_1-C_3)$-alkylsulfinyl, $(C_1-C_3)$-alkylsulfonyl, unsubstituted phenyl, substituted phenyl, unsubstituted heterocyclic radical and substituted heterocyclic radical, and, in the case of cyclic radicals, also $(C_1-C_4)$-alkyl, or is a heterocyclic radical having 3, 4, 5, 6 or 7 ring atoms and one or more atoms from the group consisting of O, N and S as a heterocyclic ring atom, preferably a saturated heterocyclic radical and preferably an-oxygen atom as the heterocyclic ring atom, the radical being unsubstituted or substituted by one or more radicals from the group consisting of halogen, $(C_1-C_3)$-alkyl and $(C_1-C_3)$-haloalkyl, $R^2$ is H, $(C_1-C_3)$-alkoxy or $(C_1-C_3)$-alkyl, $R^3$ is halogen, $(C_1-C_3)$-alkyl, $(C_1-C_3)$-alkoxy, $(C_1-C_3)$-haloalkyl, $(C_1-C_3)$-haloalkoxy, $NO_2$, CN, $NH_2$, $NHCH_3$, $N(CH_3)_2$, n is 0, 1, 2 or 3, preferably 0, 1 or 2, in particular 0 or 1, W is O or S, preferably O, X and Y independently of one another are halogen, $(C_1-C_4)$-alkyl, $(C_1-C_4)$-alkoxy or $(C_1-C_4)$-alkylthio, each of the three last-mentioned radicals being unsubstituted or substituted by one or more radicals selected from the group consisting of halogen, $(C_1-C_4)$-alkoxy and $(C_1-C_4)$-alkylthio, or are $(C_3-C_6)$-cycloalkyl, $(C_2-C_4)$-alkenyl, $(C_2-C_4)$-alkynyl, $(C_2-C_4)$-alkenyloxy, $(C_2-C_4)$-alkynyloxy or mono- or di[$(C_1-C_2)$-alkyl]amino, and Z is CH or N.

Preferred compounds of the formula (I) according to the invention are those in which $R^1$ is $(C_1-C_6)$-alkyl, $(C_2-C_6)$-alkenyl, $(C_2-C_6)$-alkynyl, $(C_3-C_6)$-cycloalkyl, $(C_4-C_8)$-cycloalkylalkyl or phenyl $(C_1-C_6)$-alkyl, each of the six last-mentioned radicals being unsubstituted or substituted by one or more radicals selected from the group consisting of halogen, such as F, Cl, Br and I, CN, $OCH_3$ and $OC_2H_5$, $OCF_3$, $SO_2CH_3$ and in the case of cyclic radicals, also $(C_1-C_3)$-alkyl, or is a radical of the formulae $A_1$ to $A_7$, in particular $A_1$, $A_2$ or $A_3$.

(A₁)

(A₂)

(A₃)

(A₄)

(A₅)

(A₆)

(A₇)

$R^2$ is H or $CH_3$, $R^3$ is halogen, $CH_3$, $C_2H_5$, $OCH_3$, $OC_2H_5$, $CF_3$, $CCl_3$, $OCF_3$, $OCHF_2$ or $N(CH_3)_2$, and n is 0, 1 or 2.

The present invention furthermore provides processes for the preparation of the compounds of the formula (I) according to the invention, which comprise a) reacting a compound of the formula (II)

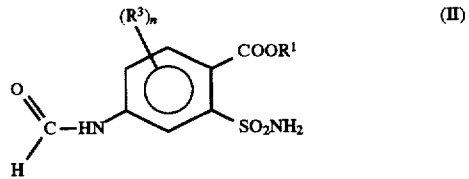

(II)

with a heterocyclic carbamate of the formula (III),

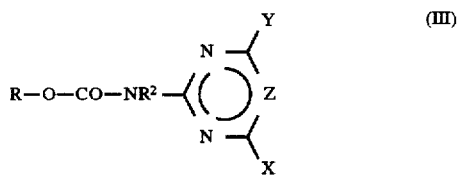

in which R is unsubstituted or substituted phenyl, or b) reacting a sulfochloride of the formula (IV)

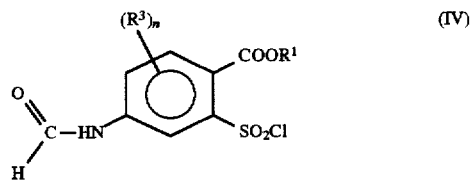

with a heterocyclic amine of the formula (V)

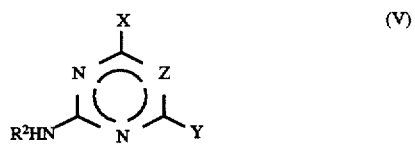

in the presence of a cyanate, e.g. an alkali metal cyanate such as sodium or potassium cyanate, or c) formylating a sulfonylurea of the formula (VI)

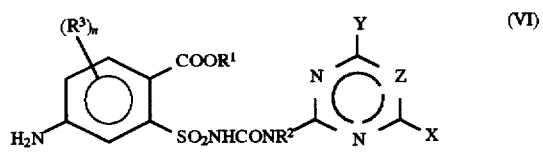

or d) reacting a sulfonamide of the formula (II) with a (thio)isocyanate of the formula (VII) in the presence of a suitable base

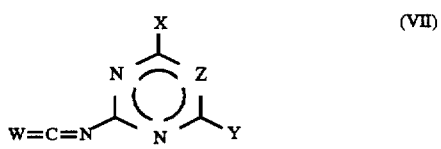

where in the above formulae (II) to (VII) the radicals $R^1$, $R^2$, $R^3$, W, X, Y and Z and also the index n are as defined in formula (I) and in the process variants a), b) and c) compounds are first obtained in which W is an oxygen atom.

The reaction of the compounds of the formulae (II) and (III) is preferably carried out in base-catalyzed form in inert solvents, such as e.g. dichloromethane, acetonitrile, dioxane, dimethylformamide (DMF), dimethylacetamide or tetrahydrofuran (THF), at temperatures from −10° C. up to the boiling point of the respective solvent. The bases used here are, for example, organic amine bases such as 1,8-diazabicyclo[5.4.0]undec-7-ene (DBU), triethylamine, or alternatively hydroxides, such as e.g. sodium or potassium hydroxide, or alkoxides, such as e.g. sodium methoxide, potassium tert-butoxide or sodium phenoxide, or carbonates, such as e.g. sodium or potassium carbonate (cf. e.g. EP-A-44807).

The sulfonamides of the formula (II) are novel and likewise the subject of this invention. They can be prepared analogously to known processes, e.g. via the formylation of corresponding aminophenylsulfonamides optionally containing protective groups.

The carbamates required for the reaction are known from the literature or can be prepared analogously to known processes (cf. EP-A-70804; U.S. Pat. No. 4,480,101; EP-A-562575; EP-A-562576).

The reaction of the sulfochlorides (IV) with the aminoheterocycles of the formula (V) and cyanates such as sodium cyanate and potassium cyanate is carried out e.g. in aprotic solvents, such as e.g. acetonitrile, if appropriate in the presence of bases, e.g. 0.5 to 2 equivalents of base, or in basic aprotic solvents at temperatures between −10° and 100° C., preferably between −10° and 60° C., in particular at 15° to 40° C. A suitable base or basic aprotic solvents are e.g. pyridine, picoline or lutidine or a mixture of these (cf. U.S. Pat. No. 5,157,119).

The reaction (formylation) of sulfonyl ureas of the formula (VI) to give the compounds of the formula (I) is carried out, for example, using the mixed anhydride from formic and acetic acid at temperatures from −10° to 60° C., preferably at 0° to 40° C., either in substance or in inert solvents such as e.g. dichloromethane, acetonitrile or ethyl acetate.

The reaction of the sulfonamides of the formula (II) with a (thio)isocyanate of the formula (VII) is carried out analogously to processes known from the literature (e.g. EP-A-232067, EP-A-166516) at −10° to 150° C., preferably 20° to 100° C., in an inert solvent, such as e.g. acetone or acetonitrile, in the presence of a suitable base, such as e.g. triethylamine or potassium carbonate.

The compounds of the formula (I) according to the invention have an excellent herbicidal activity against a broad spectrum of economically important monocotyledon and dicotyledon harmful plants. The active substances also act efficiently on perennial weeds which produce shoots from rhizomes, root stocks or other perennial organs and which are difficult to control. In this context, it does not matter whether the substances are applied before sowing, pre-emergence or post-emergence. Specifically, examples may be mentioned of some representatives of the monocotyledon and dicotyledon weed flora which can be controlled by the compounds according to the invention, without the enumeration being taken to mean a restriction to certain species.

Examples of weed species on which the active substance acts efficiently are, from amongst the monocotyledon weed species, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species. In the case of the dicotyledon weed species, the range of action extends to species such as, for example, Galium, Viola, Veronica, Lamium, Stellaria, Amaranthus, Sinapis, Ipomoea, Matricaria, Abutilon and Sida from amongst the annuals, and Convolvulus, Cirsium, Rumex and Artemisia in the case of the perennial weeds.

The active substances according to the invention also effect an outstanding control of weeds which occur under the specific conditions of rice growing, such as, for example, Sagittaria, Alisma, Eleocharis, Scirpus and Cyperus.

If the compounds according to the invention are applied to the soil surface before germination, then the weed seedlings are either prevented completely from emerging, or the weeds grow until they have reached the cotyledon stage but then their growth stops and, eventually, after three to four weeks have elapsed, they die completely.

When the active substances are applied post-emergence to the green parts of the plants, growth stops equally drastically a very short time after treatment and the weed plants remain at the stage of growth at the time of application, or they die completely after a certain time, so that in this manner competition by the weeds, which is harmful to the crop plants, is eliminated at a very early stage and in a sustained manner.

Even though the compounds according to the invention have an excellent herbicidal activity against monocotyledon and dicotyledon weeds, crop plants of economically important crops, such as, for example, wheat, barley, rye, rice, maize, sugar beet, cotton and soya, are damaged only to a negligible extent, or not at all. For these reasons, the present compounds are highly suitable for selectively controlling undesired vegetation in crops of agriculturally useful plants.

Moreover, the substances according to the invention exhibit outstanding growth-regulating properties in crop plants. They engage in the plant metabolism in a regulating manner and can thus be used for targeted plant constituent control and for facilitating harvesting, for example by provoking desiccation and stunted growth. Moreover, they are also suitable for generally controlling and inhibiting undesirable vegetative growth, without destroying the plants at the same time. Inhibition of the vegetative growth plays an important role in a large number of monocotyledon and dicotyledon crops, since it allows lodging to be reduced or prevented completely.

The compounds according to the invention can be used in the customary preparations in the form of wettable powders, emulsifiable concentrates, sprayable solutions, dusts or granules. The invention therefore also provides herbicidal and plant growth-regulating compositions comprising the compounds of the formula (I).

The compounds of the formula (I) can be formulated in a variety of ways, as determined by the prevailing biological and/or chemical-physical parameters. The following possibilities are therefore suitable for formulation: wettable powders (WP), water-soluble powders (SP), water-soluble concentrates, emulsifiable concentrates (EC), emulsions (EW) such as oil-in-water and water-in-oil emulsions, sprayable solutions, suspension concentrates (SC), oil- or water-based dispersions, oil-miscible solutions, capsule suspensions (CS), dusts (DP), seed-dressing products, granules for broadcasting and soil application, granules (GR) in the form of microgranules, spray granules, coating granules and adsorption granules, water-dispersible granules (WG), water-soluble granules (SC), ULV formulations, microcapsules and waxes.

These individual formulation types are known in principle and are described, for example, in: Winnacker-Küchler, "Chemische Technologie" [Chemical Technology], Volume 7, C. Hauser Verlag Munich, 4th ed., 1986, Wade van Valkenburg, "Pesticide Formulations", Marcel Dekker, N.Y., 1973; K. Martens, "Spray Drying" Handbook, 3rd ed. 1979, G. Goodwin Ltd. London.

The formulation auxiliaries required, such as inert materials, surfactants, solvents and other additives, are also known and are described, for example, in: Watkins, "Handbook of Insecticide Dust Diluents and Carriers", 2nd ed., Darland Books, Caldwell N.J., H.v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-Active Ethylene Oxide Adducts], Wiss. Verlagsgesell., Stuttgart 1976; Winnacker-Küchler, "Chemische Technologie" [Chemical Technology], Volume 7, C. Hauser Verlag Munich, 4th ed. 1986.

Combinations with other pesticidally active substances, such as, for example, insecticides, acaricides, other herbicides, fungicides, safeners, fertilizers and/or growth regulators, may also be prepared on the basis of these formulations, for example in the form of a readymix or a tank mix.

Wettable powders are preparations which are uniformly dispersible in water and which, besides the active substance, also comprise ionic and/or non-ionic surfactants (wetting agents, dispersants), for example polyethoxylated alkylphenols, polyethoxylated fatty alcohols, polyethoxylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the herbicidal active substances are ground finely, for example in customary apparatus such as hammer mills, blower mills and air-jet mills, and simultaneously or subsequently mixed with the formulation auxiliaries.

Emulsifiable concentrates are prepared by dissolving the active substance in an organic solvent, for example butanol, cyclohexanone, dimethylformamide, xylene or else higher-boiling aromatics or hydrocarbons or mixtures of the organic solvents, with addition of one or more ionic and/or non-ionic surfactants (emulsifiers). Examples of emulsifiers which can be used are: calcium alkylarylsulfonates, such as calcium dodecylbenzenesulfonate, or non-ionic emulsifiers such as fatty acid polyglycol esters, alkylaryl polyglycol ethers, fatty alcohol polyglycol ethers, propylene oxide/ethylene oxide condensation products, alkyl polyethers, sorbitan esters, such as, for example, sorbitan fatty acid esters or polyoxyethylene sorbitan esters, such as, for example, polyoxyethylene sorbitan fatty acid esters.

Dusts are obtained by grinding the active substance with finely divided solid substances, for example talc, natural clays such as kaolin, bentonite or pyrophyllite, or diatomaceous earth.

Suspension concentrates can be oil- or water-based. They can be prepared for example by wet grinding using commercially available bead mills and, if appropriate, addition of surfactants as already mentioned above for example in the case of the other formulation types.

Emulsions, for example oil-in-water emulsions (EW), can be prepared for example by means of stirrers, colloid mills and/or static mixtures using aqueous organic solvents and, if appropriate, surfactants as already mentioned above for example in the case of other formulation types.

Granules can be prepared either by spraying the active substance onto adsorptive, granulated inert material or by applying active substance concentrates to the surface of carriers such as sand, kaolinites or granulated inert material, by means of binders, for example polyvinyl alcohol, sodium polyacrylate or else mineral oils. Suitable active substances can also be granulated in the manner which is customary for the preparation of fertilizer granules, if desired in the form of a mixture with fertilizers.

As a rule, water-dispersible granules are prepared by the customary processes, such as spray-drying, fluidized-bed granulation, disk granulation, mixing using high-speed stirrers, and extrusion without solid inert material.

As a rule, the agrochemical preparations comprise 0.1 to 99% by weight, in particular 0.1 to 95% by weight, of active substance of the formula (I).

In wettable powders, the active substance concentration is, for example, approximately 10 to 90% by weight, the remainder to 100% by weight being composed of customary formulation components. In the case of emulsifiable concentrates, the active substance concentration can be approximately 1 to 90, preferably 5 to 80, % by weight. Formulations in the form of dusts comprise 1 to 30, preferably, in most cases, 5 to 20% by weight of active substance, sprayable solutions approximately 0.05 to 80, preferably 2 to 50, % by weight of active substance. In the case of water-dispersible granules, the active substance content depends partly on whether the active compound is in solid or liquid form and on which granulation auxiliaries, fillers and the like are being used. In the case of the water-dispersible granules, the active substance content is, for example, between 1 and 95% by weight, preferably between 10 and 80% by weight.

In addition, the abovementioned formulations of active substance comprise, if appropriate, the adhesives, wetting agents, dispersants, emulsifiers, penetrants, preservatives, antifreeze agents, solvents, fillers, carriers, colorants, antifoams, evaporation inhibitors and pH and viscosity regulators which are customary in each case.

Components which can be used in combination with the active substances according to the invention in mixed formulations or in tank mix are, for example, known active substances, as they are described, for example, in Weed Research 26, 441–445 (1986), or "The Pesticide Manual", 10th edition, The British Crop Protection Council and the Royal Society of Chemistry, 1994, England, and the literature cited therein. Examples of active substances which may be mentioned as herbicides which are known from the literature and which can be combined with the compounds of the formula (I) are the following (note: either the common names in accordance with the International Organization for Standardization (ISO) or the chemical name, if appropriate together with a customary code number, of the compounds are given): acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazin; aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; carbetamide; CDAA, i.e. 2-chloro-N,N-di-2-propenylacetamide; CDEC, i.e. chloroallyl diethyldithiocarbamate; CGA 184927, i.e. 2-[4-[(5-chloro-3-fluoro-2-pyridinyl)-oxy]phenoxy]propanoic acid and its 2-propynyl ester; chlomethoxyfen; chloramben; chlorazifop-butyl, pirifenopbutyl; chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clomazone; clomeprop; cloproxydim; clopyralid; cyanazine; cycloate; cycloxydim; cycluron; cyperquat; cyprazine; cyprazole; 2,4-DB; dalapon; desmedipham; desmetryn; di-allate; dicamba; dichlobenil; dichlorprop; diclofop-methyl; diethatyl; difenoxuron; difenzoquat; diflufenican; dimefuron; dimethachlor; dimethametryn; dimethazone, clomazon; dimethipin; dimetrasulfuron, cinosulfuron; dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-3H-pyrazole-4-carboxamide; endothal; EPTC; esprocarb; ethalfluralin; ethametsulfuronmethyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; F6285, i.e. 1-[5-(N-methylsulfonyl)amino-2,4-dichlorophenyl]-3-methyl-4-difluoromethyl-1,2,4-triazol-5-one; fenoprop; fenoxan, s. clomazon; fenoxaprop-ethyl; fenuron; flampropmethyl; flazasulfuron; fluazifop and its ester derivatives; fluchloralin; flumetsulam; N-[2,6-difluorophenyl]-5-methyl-(1,2,4)-triazolo[1,5a]pyrimidine-2-sulfonamide; flumeturon; flumipropyn; fluorodifen; fluoroglycofen-ethyl; fluridone; flurochloridone; fluroxypyr; flurtamone; fomesafen; fosamine; furyloxyfen; glufosinate; glyphosate; halosafen; haloxyfop and its ester derivatives; hexazinone; Hw 52, i.e. N-(2,3-dichlorophenyl)-4-(ethoxymethoxy)benzamide; imazamethabenz-methyl; imazapyr; imazaquin; imazethamethapyr; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyldaimuron; metobromuron; metolachlor; metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiazon; oxyfluorfen; paraquat; pebulate; pendimethalin; perfluidone; phenmedipham; phenisopharm; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its ester derivatives; propazine; propham; propyzamide; prosulfalin; prosulfocarb; prynachlor; pyrazolinate; pyrazon; pyrazosulfuron-ethyl; pyrazoxyfen; pyridate; quinclorac; quinmerac; quinofop and its ester derivatives, quizalofop and its ester derivatives; quizalofop-ethyl; quizalofop-p-tefuryl; renriduron; daimuron; S 275, i.e. 2-[4-chloro-2-fluoro-5-(2-propynyloxy)phenyl]-4,5,6,7-tetrahydro-2H-indazole; S 482, i.e. 2-[7-fluoro-3,4-dihydro-3-oxo-4-(2-propynyl)-2H-1,4-benzoxazin-6-yl]-4,5,6,7-tetrahydro-1H-isoindole-1,3(2H)-dione; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulfometuron-methyl; sulfazuron; flazasulfuron; TCA; tebutam; tebuthiuron; terbacil; terbucarb; terbuchlor; terbumeton; terbuthylazine; terbutryn; TFH 450, i.e. N,N-diethyl-3-1[(2-ethyl-6-methylphenyl)sulfonyl]-1H-1, 2,4-triazole-1-carboxamide; thiazafluron; thifensulfuron-methyl; thiobencarb; tiocarbazil; tralkoxydim; tri-allate; triasulfuron; triazofenamide; tribenuronmethyl; triclopyr; tridiphane; trietazine; trifluralin; trimeturon; vernolate; WL 110547, i.e. 5-phenoxy-1-[3-(trifluoromethyl)phenyl]-1H-tetrazole.

For use, the formulations, which are in commercially available form, are, if appropriate, diluted in the customary manner, for example using water in the case of wettable powders, emulsifiable concentrates, dispersions and water-dispersible granules, and these dilute mixtures are subsequently applied to the plants, parts of plants or the agriculturally or industrially exploited soil on which the plants stand or in which they grow or lie as seed. Preparations in the form of dusts, granules for soil application or broadcasting, as well as sprayable solutions are conventionally not diluted any further with inert substances prior to use.

The application rate required of the compounds of the formula (I) varies with the external conditions such as, inter alia, temperature, humidity and the nature of the herbicide used. It can vary within wide limits, for example between 0.001 and 10.0 kg/ha or more of active ingredient, but it is preferably between 0.005 and 5 kg/ha.

A. CHEMICAL EXAMPLES

A.1) N-[(4,6-Dimethoxypyrimidin-2-yl)aminocarbonyl]-5-formylamino-2-methoxycarbonylbenzenesulfonamide (Table 1, Ex. 1)

1.30 g of 5-formylamino-2-methoxycarbonylbenzenesulfonamide and 1.40 g of 4,6-dimethoxy-2-phenoxycarbonylaminopyrimidine are suspended in 15 ml of acetonitrile and treated at 0° C. with 2.3 ml of DBU. After 18 hours, the reaction solution is concentrated. The residue is taken up in water and washed with diethyl ether. After careful acidification of the aqueous phase with concentrated hydrochloric acid (pH=1 to 2) at 0° C., the deposited sulfonyl urea, is stirred with methanol and diisopropyl ether. 0.91 g of the desired sulfonyl urea are thus obtained; mass spectrum (CI): (M+1)=440.

A.2 N-[(4,6-Dimethoxypyrimidin-2-yl)aminocarbonyl]-5-formylamino-2-n-propoxycarbonylbenzenesulfonamide (Table 1, Ex. 15)

1.50 g of 5-formylamino-2-propoxycarbonylbenzenesulfonamide, 1.59 g of 4,6-dimethoxy-2-phenoxycarbonylaminopyrimidine and 1.8 ml of DBU in 30 ml of acetonitrile are reacted analogously to Chemical Example A.1; Yield: 1.9 g, M.p.: 151° to 153° C. (dec.); Mass spectrum (CI):(M+1)=468

A.3 N-[(4,6-Dimethoxypyrimidin-2-yl)aminocarbonyl]-5-formylamino-2-ethoxycarbonylbenzenesulfonamide (Table 1, Ex. 9)

1.00 g of 5-formylamino-2-ethoxycarbonylbenzenesulfonamide, 1.11 g of 4,6-dimethoxy-2-phenoxycarbonylaminopyrimidine and 0.82 ml of DBU in acetonitrile are reacted analogously to Chemical Example A.1; Yield: 1.00 g, M.p.: 113° to 118° C. (dec.), Mass spectrum (CI):(M+1) =454

The compounds described in Table 1 below are obtained analogously.

The following abbreviations are used in Table 1:

No.=Example No.
M.p.=Melting point
Me=methyl
Et=ethyl
Pr="Pr=n-propyl
$^i$Pr=i-propyl
$^c$Pr=cyclopropyl
(dec.)=decomposition

TABLE 1

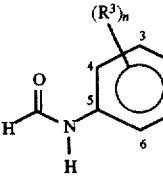

| No. | $R^1$ | $R^2$ | $(R^3)_n$ | X | Y | Z | M.p. [°C.] |
|---|---|---|---|---|---|---|---|
| 1 | Me | H | — | OMe | OMe | CH | |
| 2 | Me | H | — | OMe | Me | CH | |
| 3 | Me | H | — | Me | Me | CH | |
| 4 | Me | H | — | Cl | OMe | CH | |
| 5 | Me | H | — | Me | OMe | N | |
| 6 | Me | H | — | OMe | OMe | N | |
| 7 | Me | H | — | NMe$_2$ | OCH$_2$CF$_3$ | N | |
| 8 | Me | Me | — | OMe | Me | N | |
| 9 | Et | H | — | OMe | OMe | CH | 113–118 (decomp.) |
| 10 | Et | H | — | OMe | Me | CH | |
| 11 | Et | H | — | Me | Me | CH | |
| 12 | Et | H | — | Cl | OMe | CH | |
| 13 | Et | H | — | OMe | Me | N | |
| 14 | Et | H | — | OMe | OMe | N | |
| 15 | $^n$Pr | H | — | OMe | OMe | CH | 151–153 (decomp.) |
| 16 | $^n$Pr | H | — | OMe | Me | CH | |
| 17 | $^n$Pr | H | — | Me | Me | CH | |
| 18 | $^n$Pr | H | — | OMe | Cl | CH | |
| 19 | $^n$Pr | H | — | OMe | Me | N | |
| 20 | $^n$Pr | H | — | OMe | OMe | CH | |
| 21 | $^i$Pr | H | — | OMe | Me | CH | |
| 22 | $^i$Pr | H | — | Me | Me | CH | |
| 23 | $^i$Pr | H | — | Cl | OMe | CH | |
| 24 | $^i$Pr | H | — | OMe | Me | N | |
| 25 | $^c$Pr | H | — | OMe | OMe | CH | |
| 26 | $^c$Pr | H | — | Me | Me | CH | |
| 27 | $^c$Pr | H | — | Me | OMe | CH | |
| 28 | $^c$Pr | H | — | Cl | OMe | CH | |
| 29 | CH$_2$CH=CH$_2$ | H | — | OMe | OMe | CH | |
| 30 | CH$_2$CH=CH$_2$ | H | — | Me | Me | CH | |
| 31 | CH$_2$CH=CH$_2$ | H | — | Me | OMe | CH | |
| 32 | CH$_2$CH=CH$_2$ | H | — | Cl | OMe | CH | |
| 33 | 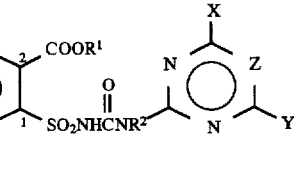 | H | — | OMe | OMe | CH | |
| 34 | (same cyclic group) | H | — | Me | Me | CH | |
| 35 | (same cyclic group) | H | — | OMe | Me | CH | |
| 36 | (same cyclic group) | H | — | OMe | Cl | CH | |
| 37 | (cyclic ether group) | H | — | OMe | OMe | CH | |
| 38 | (cyclic ether group) | H | — | Me | Me | CH | |

-continued

| No. | R¹ | R² | (R³)ₙ | X | Y | Z | M.p. [°C.] |
|---|---|---|---|---|---|---|---|
| 39 |  | H | — | OMe | OMe | CH | |
| 40 | CH₂CF₃ | H | — | OMe | OMe | CH | |
| 41 | CH₂CH₂Cl | H | — | OMe | OMe | CH | |
| 42 | CH₂CH₂OMe | H | — | OMe | OMe | CH | |
| 43 | CH₂CH₂SMe | H | — | OMe | OMe | CH | |
| 44 | CH—CH₂<br>\|  \|<br>CH₂—CH₂ | H | — | OMe | OMe | CH | |
| 45 | CH₂C≡CH | H | — | OMe | OMe | CH | |
| 46 | Me | H | 3-Me | OMe | OMe | CH | |
| 47 | Me | H | 3-F | OMe | OMe | CH | |
| 48 | Me | H | 3-NMe₂ | OMe | OMe | CH | |
| 49 | Me | H | 6-F | OMe | OMe | CH | |
| 50 | Me | H | 6-Cl | OMe | OMe | CH | |
| 51 | Me | H | 3,6-Cl₂ | OMe | OMe | CH | |
| 52 | H | H | — | OMe | OMe | CH | |
| 53 | H | H | — | OMe | Me | CH | |
| 54 | H | H | — | Me | Me | CH | |
| 55 | H | H | — | Cl | OMe | CH | |
| 56 | H | H | — | OMe | OMe | N | |
| 57 | H | H | — | Me | OMe | N | |
| 58 | Me | Me | — | OMe | OMe | CH | |
| 59 | Me | Me | — | Me | OMe | CH | |
| 60 | Me | Me | — | OMe | OMe | N | |
| 61 | H | Me | — | OMe | OMe | CH | |
| 62 | H | Me | — | OMe | Me | N | |

B. Formulation Examples a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium ligninsulfonate and 1 part by weight of sodium oleoylmethyltaurinate as wetting agent and dispersant, and grinding the mixture in a pinned-disk mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example approximately 255° to above 277° C.) and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of oxethylated nonylphenol as emulsifier.

e) Water-dispersible granules are obtained by mixing 75 parts by weight of a compound of the formula (I), 10 parts by weight of calcium ligninsulfonate, 5 parts by weight of sodium lauryl sulfate, 3 parts by weight of polyvinyl alcohol and 7 parts by weight of kaolin, grinding the mixture on a pinned-disk mill and granulating the powder in a fluidized bed by spraying on water as granulation liquid.

f) Water-dispersible granules are also obtained by homogenizing and precomminuting, in a colloid mill, 25 parts by weight of a compound of the formula (I), 5 parts by weight of sodium 2,2'-dinaphthylmethane-6,6'-disulfonate, 2 parts by weight of sodium oleoylmethyltaurinate, 1 part by weight of polyvinyl alcohol, 17 parts by weight of calcium carbonate and 50 parts by weight of water, subsequently grinding the mixture in a bead mill and atomizing and drying the resulting suspension in a spray tower by means of a single-substance nozzle.

C. Biological Examples

1. Pre-emergence activity against weeds

Seeds or rhizome pieces of monocotyledon and dicotyledon weed plants are placed in sandy loam soil in plastic pots and covered with soil. The compounds according to the invention, which are formulated as wettable powders or emulsion concentrates, are then applied to the surface of the soil cover in the form of aqueous suspensions or emulsions at an application rate of 600 to 800 l of water/ha (converted), in various dosages.

After the treatment, the pots are placed in a greenhouse and kept under good growth conditions for the weeds. After the test plants have emerged, the damage to the plants or the negative effect on the emergence was scored visually after a test period of 3 to 4 weeks had elapsed, by comparison with untreated controls. As shown by the test results, the compounds according to the invention have a good herbicidal pre-emergence activity against a wide range of grass weeds and broad-leaved weeds. For example, the compounds of Examples 1, 9 and 15 of Table 1 have a very good herbicidal activity against harmful plants such as *Alopecurus myosuroides*, *Sinapis alba*, *Chrysanthemum segetum*, *Avena sativa*, *Stellaria media*, *Echinochloa crus-galli* and *Lolium multiflorum* when applied pre-emergence at an application rate of 0.3 kg and less of active ingredient per hectare.

2. Post-emergence activity against weeds

Seeds or rhizome pieces of mono- and dicotyledon weeds are placed in sandy loam soil in plastic pots, covered with soil and grown in a greenhouse under good growth conditions. Three weeks after sowing, the test plants are treated in the three-leaf stage.

The compounds according to the invention, which are formulated as wettable powders or emulsion concentrates, are sprayed in various dosages onto the green parts of the plants at an application rate of 600 to 800 l of water/ha (converted) and, after the test plants have remained in the greenhouse for about 3 to 4 weeks under optimum growth conditions, the activity of the preparations was scored visually in comparison with untreated controls. The compositions according to the invention also have a good herbicidal post-emergence activity against a wide range of economically important grass weeds and broad-leaved weeds. For example, the compounds of Examples 1, 9 and 15 of Table 1 have a very good herbicidal activity against harmful plants such as *Alopecurus myosuroides*, *Sinapis alba*, *Stellaria media*, *Echinochloa crus-galli*, *Lolium multiflorum*, *Chrysanthemum segetum* and *Avena sativa* when applied post-emergence at an application rate of 0.3 kg or less of active ingredient per hectare.

3. Tolerance by crop plants

In further greenhouse experiments, seeds of a substantial number of crop plants and weeds are placed in sandy loam soil and covered with soil. Some of the pots are treated immediately as described under Section 1 while the remaining pots are placed in the greenhouse until the plants have developed two to three true leaves and then sprayed with various dosages of the substances of the formula (I) according to the invention, as described in Section 2. Visual scoring four to five weeks after the application and after the plants have remained in the greenhouse reveals that the compounds according to the invention do not inflict any damage to dicotyledon crops such as, for example, soya, cotton, oilseed rape, sugar beet and potatoes when used pre- and post-emergence, even when high dosages of active substance are

What is claimed is:

1. A compound of the formula (I)

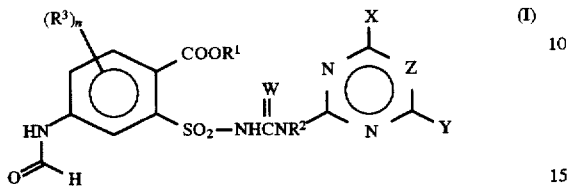

wherein

R$^1$ is H, (C$_1$–C$_{12}$)-alkyl, (C$_2$–C$_{12}$)-alkenyl or (C$_2$–C$_{12}$)-alkynyl, (C$_3$–C$_6$)-cycloalkyl or phenyl, each of the last mentioned alkyl-containing radicals being unsubstituted or substituted by one or more radicals selected from the group consisting of halogen, CN, (C$_1$–C$_3$)-alkoxy, (C$_1$–C$_3$)-haloalkoxy, (C$_3$–C$_6$)-cycloalkyl, (C$_1$–C$_3$)-alkylthio, (C$_1$–C$_3$)-alkylsulfinyl, (C$_1$–C$_3$)-alkylsulfonyl and phenyl, which is unsubstituted or substituted by one or more identical or different radicals selected from the group consisting of halogen, (C$_1$–C$_4$)-alkyl, (C$_1$–C$_4$)-alkoxy, (C$_1$–C$_4$)-haloalkyl, (C$_1$–C$_4$)-haloalkoxy, nitro and cyano, and a saturated heterocyclic radical having 3 to 7 ring atoms and having 1 hetero ring atom from the group consisting of N, O and S, or a heterocyclic radical selected from piperazinyl dioxolanyl and morpholinyl the radical being unsubstituted or substituted by one or more radicals from the group consisting of halogen, (C$_1$–C$_3$)-alkyl, (C$_1$–C$_3$)-haloalkyl and oxo, and in the case of cyclic radicals also (C$_1$–C$_4$)-alkyl and (C$_1$–C$_4$)-haloalkyl, or is a saturated heterocyclic radical having 3 to 7 ring atoms and having 1 hetero ring atom from the group consisting of N, O and S, or a heterocyclic radical selected from piperazinyl, dioxolanyl and morpholinyl the radical being unsubstituted or substituted by one or more radicals from the group consisting of halogen, (C$_1$–C$_3$)-alkyl, (C$_1$–c$_3$)-haloalkyl and oxo, R$^2$ is H, (C$_1$–C$_6$)-alkyl or (C$_1$–C$_6$)-alkoxy, R$^3$ is halogen, (C$_1$–C$_6$)-alkyl, (C$_1$–C$_6$)-haloalkyl, (C$_1$–C$_6$)-alkoxy, (C$_1$–C$_6$)-haloalkoxy, NO$_2$, CN, NH$_2$ or mono- or di-(C$_1$–C$_4$)-alkylamino, each independently of other radicals R$^3$ if n is 2 or 3, n is 0, 1, 2 or 3, W is an oxygen or sulfur atom, p1 X and Y independently of one another are halogen, (C$_1$–C$_6$)-alkyl, (C$_1$–C$_6$)-alkoxy or (C$_1$–C$_6$)-alkylthio, each of the three last-mentioned radicals being unsubstituted or substituted by one or more radicals selected from the group consisting of halogen, (C$_1$–C$_4$)-alkoxy and (C$_1$–C$_4$)-alkylthio, or are (C$_3$–C$_6$)-cycloalkyl, (C$_2$–C$_6$)-alkenyl, (C$_2$–C$_6$)-alkynyl, (C$_2$–C$_6$)-alkenyloxy, (C$_2$–C$_6$)-alkynyloxy, mono- or di-[(C$_1$–C$_4$)-alkyl]-amino, and Z is CH.

2. A compound as claimed in claim 20, wherein

R$^1$ is H, (C$_1$–C$_6$)-alkyl, (C$_2$–C$_6$)-alkenyl or (C$_2$–C$_6$)-alkynyl or (C$_3$–C$_6$)-cycloalkyl, each of the four last-mentioned radicals being unsubstituted or substituted by one or more radicals selected from the group consisting of halogen, CN, (C$_1$–C$_3$)-alkoxy, (C$_1$–C$_3$)-haloalkoxy, (C$_3$–C$_6$)-cycloalkyl, (C$_1$–C$_3$)-alkylthio, (C$_1$–C$_3$)-alkylsulfinyl, (C$_1$–C$_3$)-alkylsulfonyl and phenyl, which is unsubstituted or substituted by one or more identical or different radicals selected from the group consisting of halogen, (C$_1$–C$_4$)-alkyl, (C$_1$–C$_4$)-alkoxy, (C$_1$–C$_4$)-haloalkyl, (C$_1$–C$_4$)-haloalkoxy, nitro and cyano, and a saturated heterocyclic radical having 3 to 7 ring atoms and 1 heteroatom from the group consisting of N, O and S, the radical being unsubstituted or substituted by one or more radicals from the group consisting of halogen, (C$_1$–C$_3$)-alkyl and (C$_1$–C$_3$)-haloalkyl, and in the case of cyclic radicals also (C$_1$–C$_4$)-alkyl.

R$^2$ is H, (C$_1$–C$_3$)-alkyl or (C$_1$–C$_3$)-alkoxy,

R$^3$ is halogen, (C$_1$–C$_3$)-alkyl, (C$_1$–C$_3$)-alkoxy, (C$_1$–C$_3$)-haloalkyl, (C$_1$–C$_3$)-haloalkoxy, NO$_2$, CN, NH$_2$ or NHCH$_3$ or N(CH$_3$)$_2$, each independently of other radicals R$^3$ if n is 2 or 3, n is 0, 1, 2 or 3, W is an oxygen or sulfur atom, X and Y independently of one another are halogen, (C$_1$–C$_4$)-alkyl, (C$_1$–C$_4$)-alkoxy or (C$_1$–C$_4$)-alkylthio, each of the three last-mentioned radicals being unsubstituted or substituted by one or more radicals selected from the group consisting of halogen, (C$_1$–C$_4$)-alkoxy and (C$_1$–C$_4$)-alkylthio, or are (C$_3$–C$_6$)-cycloalkyl (C$_2$–C$_4$)-alkenyl, (C$_2$–C$_4$)-alkynyl, (C$_2$–C$_4$)-alkenyloxy, (C$_2$–C$_4$)-alkynyloxy, mono- or di-[(C$_1$–C$_4$)-alkyl]-amino, and Z is CH.

3. A compound of the formula (I) as claimed in claim 2 wherein

R$^1$ is (C$_1$–C$_6$)-alkyl, (C$_2$–C$_6$)-alkenyl, (C$_2$–C$_6$)-alkynyl, (C$_3$–C$_6$)-cycloalkyl, (C$_4$–C$_8$)-cycloalkylalkyl or phenyl (C$_1$–C$_6$)-alkyl, each of the six last-mentioned radicals being unsubstituted or substituted by one or more radicals selected from the group consisting of halogen, CN, OCH$_3$, OC$_2$H$_5$, OCF$_3$ and SO$_2$CH$_3$ and in the case of cyclic radicals, also (C$_1$–C$_3$)-alkyl.

or is a radical of the formulae A$_1$ to A$_7$

-continued

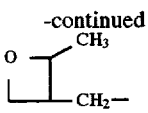
(A₇)

$R^2$ is H or $CH_3$, $R^3$ is halogen, $CH_3$, $C_2H_5$, $OCH_3$, $OC_2H_5$, $CF_3$, $CCl_3$, $OCF_3$, $OCHF_2$ or $N(CH_3)_2$, and n is 0, 1 or 2.

4. A compound of the formula (I), or a salt thereof, as defined in claim 1, wherein $R^1$ is methyl, $R^2$ is hydrogen, n is zero, X is methoxy, Y is methoxy and Z is CH.

5. A compound of the formula (I), or a salt thereof, as defined in claim 1, wherein $R^1$ is methyl, $R^2$ is hydrogen, n is zero, X is methoxy, Y is methyl and Z is CH.

6. A compound of the formula (I), or a salt thereof, as defined in claim 1, wherein $R^1$ is methyl, $R^2$ is hydrogen, n is zero, X is methyl, Y is methyl and Z is CH.

7. A compound of the formula (I), or a salt thereof, as defined in claim 1, wherein $R^1$ is methyl, $R^2$ is hydrogen, n is zero, X is chloro, Y is methoxy and Z is CH.

8. A compound of the formula (I), or a salt thereof, as defined in claim 1, wherein $R^1$ is ethyl, $R^2$ is hydrogen, N is zero, X is methoxy, Y is methoxy and Z is CH.

9. A compound of the formula (I), or a salt thereof, as defined in claim 1, wherein $R^1$ is ethyl, $R^2$ is hydrogen, n is zero, X is methoxy, Y is methyl and Z is CH.

10. A compound of the formula (I), or a salt thereof, as defined in claim 1, wherein $R^1$ is ethyl, $R^2$ is hydrogen, n is zero, X is methyl, Y is methyl and Z is CH.

11. A compound of the formula (I), or a salt thereof, as defined in claim 1, wherein $R^1$ is ethyl, $R^2$ is hydrogen, n is zero, X is chloro, Y is methoxy and Z is CH.

12. A compound of the formula (I), or a salt thereof, as defined in claim 1, wherein $R^1$ is isopropyl, $R^2$ is hydrogen, n is zero, X is methoxy and Z is CH.

13. A compound of the formula (I), or a salt thereof, as defined in claim 1, wherein $R^1$ is isopropyl, $R^2$ is hydrogen, n is zero, X is methoxy, Y is methyl and Z is CH.

14. A compound of the formula (I), or a salt thereof, as defined in claim 1, wherein $R^1$ is isopropyl, $R^2$ is hydrogen, n is zero, X is methyl, Y is methyl and Z is CH.

15. A compound of the formula (I), or a salt thereof, as defined in claim 1, wherein $R^1$ is isopropyl, $R^2$ is hydrogen, n is zero, X is chloro, Y is methoxy and Z is CH.

16. A herbicidal or plant growth-regulating composition, which comprises an effective amount of one or more compound of the formula (I), as claimed in claim 1, and formulation auxiliaries conventionally used in crop protection.

17. A method of controlling harmful plants or of regulating the growth of plants, which comprises applying an effective amount of one or more compound of the formula (I) as claimed in claim 1 to the harmful plants or plants, the seeds of these plants or the area on which the plants grow.

* * * * *